United States Patent [19]

Bridle et al.

[11] Patent Number: 4,818,274
[45] Date of Patent: Apr. 4, 1989

[54] METHOD AND COMPOSITION FOR REGULATING THE FLOWERING OF PLANTS

[75] Inventors: Kenneth A. Bridle; Mordecai J. Jaffe, both of Winston-Salem, N.C.

[73] Assignee: Wake Forest University, Winston-Salem, N.C.

[21] Appl. No.: 812,248

[22] Filed: Dec. 23, 1985

[51] Int. Cl.[4] ............................................. A01N 37/04
[52] U.S. Cl. ..................................... 71/106; 560/191
[58] Field of Search .......................... 71/106; 560/191; 514/547

[56] References Cited

U.S. PATENT DOCUMENTS

| | | | |
|---|---|---|---|
| 2,322,761 | 6/1943 | Lontz | 71/77 |
| 2,341,867 | 2/1944 | Hitchcook et al. | 71/106 |
| 2,363,325 | 11/1944 | Hitchcock et al. | 71/106 |
| 2,603,560 | 7/1952 | Stewart et al. | 71/106 |
| 2,610,117 | 9/1952 | Hopf et al. | 71/106 |
| 2,979,538 | 4/1961 | Wotiz | 71/106 |
| 3,338,702 | 8/1967 | Newcomer et al. | 71/106 |
| 3,555,160 | 1/1971 | Gier et al. | 71/106 |
| 3,810,750 | 5/1974 | Davidson et al. | 71/106 |
| 3,900,307 | 8/1975 | Abramitis | 71/106 |
| 4,071,348 | 1/1978 | Abramitis | 71/106 |

FOREIGN PATENT DOCUMENTS 3321529 12/1984 Fed. Rep. of Germany.
795018 5/1958 United Kingdom .... 47/DIG. 0.005

OTHER PUBLICATIONS

Ditgens et al., "Plant Growth-Regulating, etc.", CA 102: 74218y 1985.
Inden et al., "Damage on Crops by Gases, etc", Mie Daigaku Nogakubu Gakujutsu Hokoku 50 (1975).
Jan A. D. Zeevaart, Ann. Rev. Plant Physiol. 27, 321 (1976).
M. Kh. Chailakhyan, Plant Growth Substances, P. F. Wareing, Ed., 645 (1982).
Daphne Vince-Prue, Bryan Thomas and K. E. Cockshull, Light and the Flowering Process (Academic Press, London, 1984).
F. B. Salisbury and C. W. Ross, Plant Physiology, 3, 426 (1985).
E. G. Groenewald, J. H. Visser and N. Grobblelaar, S. Afr. Tydskr. Plantk. 2(1), 82 (1983).
Charles F. Cleland and Alfred Ajami, Plant Physiol. 54, 904 (1974).
R. J. Pryce, Phytochemistry, 11, 1911 (1972).
Masana Noma, Naoko Koike, Minoru Sano and Nobumaro Kawashima, Plant Physiol. 75, 257 (1984).
Miriam Aharoni, Eliezer E. Goldschmidt and Abraham H. Halevy, J. Plant Physiol. 120, 145 (1985).
Tokutaro Inden and Shoji Tachibana, Damage of Crops by Gases from the Plastic Materials Under Covering Conditions, 50 (1975).
S. Sawhney, N. Sawhney and K. K. Nanda, Acta Botanica Indica 11, 198 (1983).
H. Kent Hodson and K. C. Hamner, Science 167, 384 (1969).
Richard G. Lincoln, Darwin L. Mayfield and Alan Cunningham, Science 133, 756 (1960).
Hiroshi Suge, Plant & Cell Physiol. 13, 1031 (1972).
F. Cabanne, M. A. Dalebroux, J. Martin-Tanguy and C. Martin, Physiology and Biochemistry, 539 (1981).
J. G. Purse, Journal of Experimental Botany 35, 227 (1984).

(List continued on next page.)

Primary Examiner—Glennon H. Hollrah
Assistant Examiner—Patricia L. Morris
Attorney, Agent, or Firm—Bell, Seltzer, Park & Gibson

[57] ABSTRACT

A method of delaying flowering in plants which control their flowering by producing a flowering inhibiting regulator on a seasonal basis is provided. In the method of the invention, a flowering inhibiting amount of the regulator is applied to the plant about the time in the growth cycle of the plant when the regulator is no longer produced by the plant. As a result, the duration of the inhibitory effect on the plant is prolonged. Bis (2-ethylhexyl) hexane dioate (BEHD) is disclosed as such a regulator. Also disclosed is a family of diesters of dicarboxylic acids having flowering inhibiting activity, other methods of treating plants with these compounds, and a new method of identifying flowering regulators.

7 Claims, 3 Drawing Sheets

OTHER PUBLICATIONS

F. Bangerth, *Ber. Deutsch. Bot. Ges. Bd.* 97, 257 (1984).

Masateru Shinozaki and Atsushi Takimotor, *Plant & Cell Physiol.* 24(3), 433 (1983).

Sumiko Kaihara and Atsushi Takimotor, *Plant & Cell Physiol.* 24(3), 309 (1983).

E. G. Groenewald and J. H. Visser, *Z. Pflanzenphysiol. Bd.* 88, 423 (1978).

Hiroshi Harada, *Plant Growth Regulators S.C.I. Monograph* 31, 170 (1968).

James Bonner, Erich Heftmann and Jan A. D. Zeevaart, *Plant Physiology* 38, 81 (1963).

Jan A. D. Zeevaart, *Plant Physiology* 39, 402 (1964).

Kiem Tran Thanh Van, Patrick Toubart and Alain Cousson; Alan G. Darvill, David J. Gollin, Paulanne Chelf and Peter Albersheim, *Nature* 314, 615 (1985), and attached news summary of Keith Roberts, *Nature* 314, 581 (1985).

Douglas J. C. Friend, Monique Bodson and Georges Bernier, *Plant Physiol.* 75, 1085 (1984).

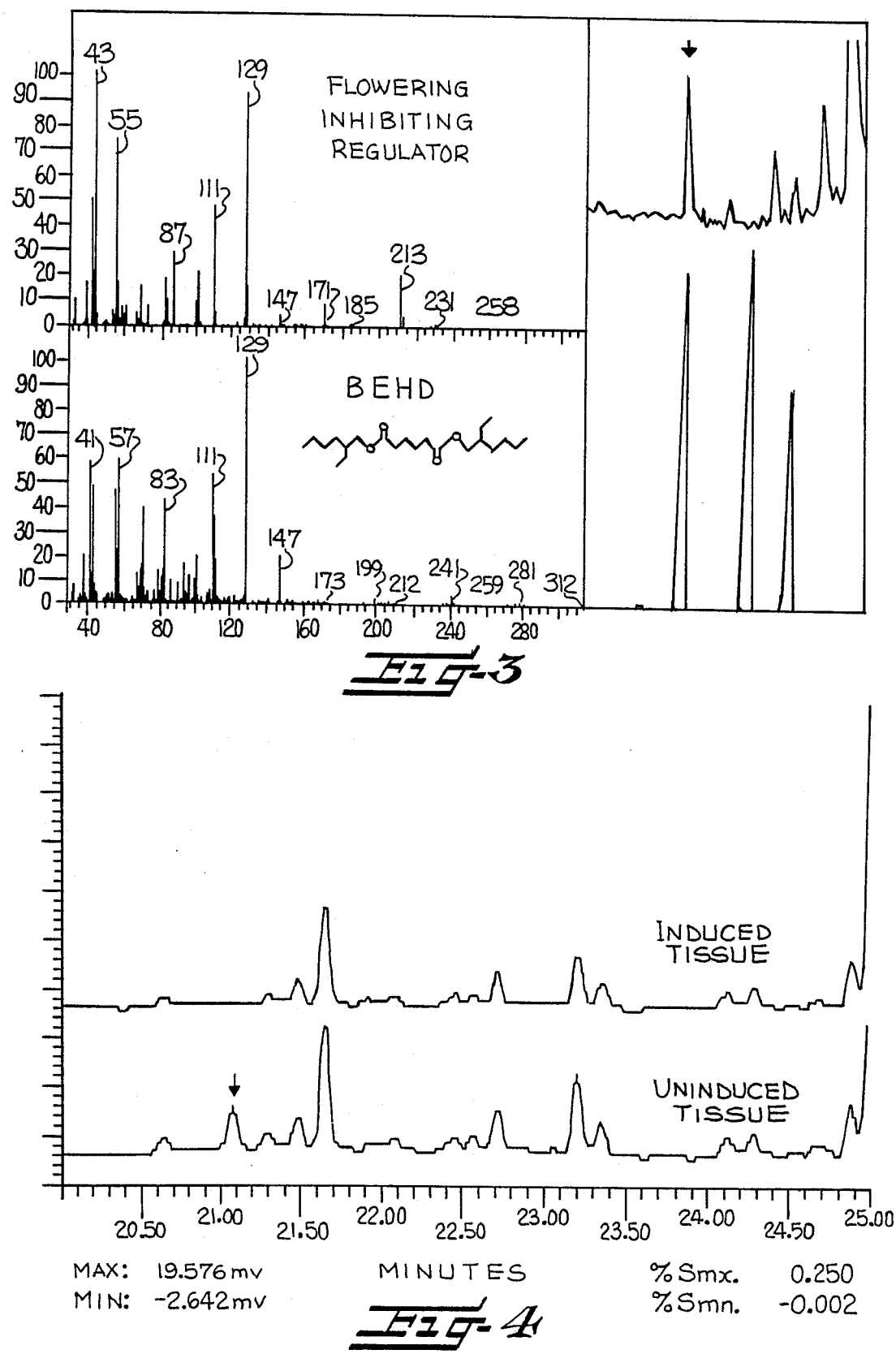

METHOD AND COMPOSITION FOR REGULATING THE FLOWERING OF PLANTS

FIELD OF THE INVENTION

This invention relates to plant growth regulation generally, and particularly relates to methods and compositions for controlling flowering in plants.

BACKGROUND OF THE INVENTION

Casual observation shows that most plants do not flower at random. In locations with a seasonal or otherwise variable climate, synchronized flowering is a spectacular event. To the farmer who faces risks such as the early flowering of crops during killing frosts, however, synchronized flowering can be a disaster.

Not surprisingly, there has been a substantial amount of basic research into how plants control flowering, and a substantial amount of applied research into methods and compounds for delaying or inhibiting flowering in plants. In spite of this research, there has not been discovered a method of inhibiting flowering in plants which takes advantage of, and manipulates, the natural flowering regulatory system of plants. Such a method would provide mankind with extremely precise and nontoxic control over the plants and crops on which he depends.

a. The Basic Research

Flowering results from evocation: a conversion of vegetative, leaf-producing buds to floral buds. Depending on the species, the signal which causes, or "induces," this conversion may come from within the plant or from a subtle blend of environmental cues. Many plants are induced to flower by the length of the day. Such plants include both short day plants (which exhibit greater flowering as days become shorter) and long day plants (which exhibit greater flowering as days become longer), but exclude day neutral plants. (Since it is actually the length of the night—not the day—which is the signal which induces flowering, it is biologically correct to refer to these plants as "long night" and "short night" plants, respectively. However, in this application the historical terminology "short day" and "long day" will be followed for consistency). Day neutral plants may be induced to flower by other factors, such as temperature, plant maturity, or an internal program.

Photoperiodic floral induction in plants takes place in the leaves, where a pigment called "phytochrome" absorbs daylight and is involved in the measurement of the length of the night. When leaves of induced plants have been grafted onto stems of deleaved, uninduced plants, the uninduced plants ("receiver" plants) will flower. The receiver plant's leaves are removed because a flowering inhibitor might be present which would only be removed by photoperiodic induction. Thus, the induction of flowering has been believed to be under the control of either, or both, of two types of flowering regulators: the DE NOVO appearance of an endogenous (naturally occurring) flowering promoting regulator or the disappearance of an endogenous flowering inhibiting regulator. A. Lang., *Ann. Rev. Plant Physiol.* 3:265 (1952). Since this theoretical analysis was published, no one has presented convincing evidence for the identity of either a flowering promoting regulator or a flowering inhibiting regulator. This has probably been because the strategy has usually been to apply crude extracts of induced plants to other, uninduced plants.

Over a thousand articles have been published on how plants regulate the flowering process. These papers are readily available, and the contents of only a few of them will be discussed below. The progress in this field has, however, recently been summarized in one leading text as follows: "There is much circumstantial evidence that flower initiation is controlled by hormones: one or more positively acting florigens and one or more negatively acting inhibitors. These substances remain to be identified." F. B. Salisbury and C. W. Ross, *Plant Physiology* 444 (3d Ed. 1985). The authors of this text further state that, of late, no major breakthroughs have appeared in this field, research has decreased noticeably, and most of those working in the art apparently feel that a temporary dead end has been reached. Id. at 446.

There have been numerous attempts to identify a flowering inhibiting regulator (we herein use the term "regulator" instead of "hormone") but none have achieved success. Pryce, *Phytochemistry* 11, 1911 (1972), suggested that Gallic acid was a natural flowering inhibitor in *Kalachoe glossfeldiana*, but Pryce's data also showed that Gallic acid was present in the leaves of flowering Kalanchoe. Pryce's conclusion has since been rejected as erroneous. J. Zeevart, Ann. Rev. Plant Physiol. 27, 321 (1976); W. W. Schwabe, *Photoperiodic Induction-Flowering Inhibiting Substances*, in *Light and the Flowering Process* (D. Vince-Prue, B. Thomas, and K. Cockshall, Ed. 1984) (hereinafter "Schwabe"). Schwabe suggests that an unidentified Oleuropein-like compound inhibits flowering in Kalanchoe. He does not propose that Oleuropein is a flowering inhibitor actually produced by the plant. Schwabe additionally suggests that 2-flavan-3-ol fractions may be involved in the inhibition of flowering in Kalanchoe, but could make no definite conclusion as to either whether or not Kalanchoe had a flowering inhibitor or the identity of that inhibitor. Moreover, Schwabe does not even suggest that Oleuropein is absent from flowering plants.

A compound which is present in a nonflowering plant, disappears from the plant when the plant has been induced to flower, and inhibits flowering when administered to plants which have been induced to flower or are otherwise capable of flowering has not yet been disclosed. Such a compound would be a flowering inhibiting regulator—a plant growth regulator specifically involved in the control of flowering. Similarly, a compound which is absent from a nonflowering plant, appears when the plant has been induced to flower, and promotes flowering when administered to plants which have not been induced to flower or are otherwise not yet capable of flowering would be a flowering promoting regulator. These compounds are to be herein contrasted with other plant growth regulators which do not have a role in the mechanisms controlling flowering, yet will have some effect on flowering when applied to plants (e.g., ethylene).

b. The Applied Research

Without a basic understanding of how plants control flowering, efforts to develop commercial flowering inhibitors have been limited to simply applying candidate compounds to plants and screening them for some effect. Representative is U.S. Pat. No. 2,341,867 to Hitchcock et al., which suggests a method of inhibiting flowering by treating buds with the synthetic auxin naphthaleneaceticacid (NAA). The specification suggests that the optimum time of treatment is before the bud starts to open, and that flower buds should generally be treated when swollen but before the color of the petals becomes distinctly visible, but does not suggest that the compound is a flowering inhibiting regulator. This method only prevents the opening of previously evoked buds, and does not prevent the conversion of vegetative buds to floral buds.

Numerous investigators have explored the use of particular compounds to regulate plant growth generally, without focusing solely on flowering. Representative of these are the following:

U.S. Pat. No. 2,603,560 to Stewart suggests a composition comprising a diester of a dicarboxylic acid in which one of the alcohol residues is an alkenyl radical for altering the growth characteristics of plants, and mentions applying the composition to plants to retard blossoming. As to this suggestion, however, the patent only explains the use of the composition for defloration, or blossom thinning, and does not teach how to use the compound to inhibit flowering.

U.S. Pat. No. 3,810,750 to Davidson et al. suggests the use of fully or partially esterified dicarboxylic acids to regulate plant growth. At least one of the esterifying groups in the compounds used is an allyl or propargyl group. The compositions are suggested as being useful for killing damaging the growing points of shoots of the plants to which they are applied.

U.S. Pat. No. 3,555,160 to Gier et al. suggests the use of chloronitrophenyl esters of polycarboxylic acids as herbicide, fungicide and nematocide. Examples of the claimed compounds include bis (2, 4 dichloro-6-nitrophenyl) adipate. The use of the compound to inhibit flowering is not even suggested.

U.S. Pat. No. 2,979,538 to Wotz discloses propynyl esters of dicarboxylic acids, and suggests that the compounds have herbicidal activity. Examples include the use of bis (2-propynyl) malonate as a herbicide, but the use of the compound to inhibit flowering is not even suggested.

Insofar as we have been able to determine, a method of inhibiting flowering which manipulates the flowering control system of plants has neither been discovered nor disclosed. The availability of such a method would provide a powerful, specific and nontoxic way to inhibit flower formation. Such a method could be used, among other purposes, to delay flowering to avoid frost damage, and to delay flowering so that plants are maintained in a vegetative state.

c. Methods of Identifying Flowering Regulators

So far as we are aware, in previously reported methods of identifying flowering regulators, crude plant extracts containing numerous compounds are screened by applying the extracts to plants or plant tissue and examining those plants or tissues for some effect (a "bioassay").

Groenewald, E. G., Visser, J. H., and Grobbelaar, N., *S. Afr. J. Bot.* 2, 82 (1983), investigated the occurrence of prostaglandin in Morning Glory seedlings by raising induced and uninduced plants, harvesting the plants, and examining extracts of the plants for prostraglandins with a radio-immunoassay kit. The authors suggest that prostaglandins had previously been found to promote flowering when applied to plant tissue, and that the concentration of prostaglandin is 20 times higher in uninduced plants than in induced plants. This procedure is, of course, limited to the detection of compounds for which a radioimmunoassay kit is available. Moreover, this procedure requires that the proposed flowering regulator be first identified by the use of a bioassay before it is shown to vary in concentration in the plant, depending on whether or not the plant has been induced to flower. As explained above, this procedure has been ineffective in advancing the understanding of flowering regulation.

d. Conclusion

Prior to the present invention, there had not yet been discovered or disclosed a flowering inhibiting regulator, nor a method of using a flowering inhibiting regulator to delay the flowering of plants, nor a method which has succeeded in identifying a flowering inhibiting regulator.

It is accordingly an object of the present invention to provide an accurate and reliable method of identifying naturally occurring flowering regulators.

A further object of the invention is to provide a method of controlling flowering by the application of such regulators.

More specific objects of our invention are to provide a reliable method of identifying flowering inhibiting regulators, and a method of inhibiting flowering by the application of such regulators.

SUMMARY OF THE INVENTION

This invention is based on our discovery that bis (2-ethylhexyl) hexane dioate (BEHD) is a naturally occurring flowering inhibiting regulator in plants. To the best of our knowledge, this is the first endogenous flowering inhibiting regulator that is a part of the mechanism regulating flowering which has been identified. By applying a regulator such as BEHD, or the biologically active compounds similar to the regulator, to a plant about the time in the growth cycle of the plant when it is no longer produced by the plant, the duration of the inhibitory effect of the regulator on the flowering process can be prolonged. As a result, the flowering of the plant can be delayed.

Also provided is a method of extracting compounds from plants which fluctuate in concentration in relation to the flowering cycle of the plant, and a method by which flowering regulators are identified. We believe our method to be the first in which any endogenous flowering regulator which is a part of the flowering mechanism has been identified without the use of a protracted initial screening step, or bioassay, as the first step. In our method, a first tissue sample is collected from a group of plants which have been induced to flower, and a second tissue sample is collected from a group of plants which have not been induced to flower. Extracts are prepared from each tissue sample, chromatograms are prepared from each extract, and the chromatograms compared to detect chemical differences in the samples. These chemicals can then be identified. Flowering inhibiting regulators identified by this method (compounds present in the uninduced plants only) are used for delaying flowering in plants by applying the regulator thereby identified to plants about the time when the regulator is no longer produced by the plants. Flowering promoting regulators identified by this method (compounds present in the induced plants only) can be used to promote flowering in plants by applying the regulator thereby identified to the plant before the time when the regulator is produced by the plant.

This procedure will probably reveal some compounds which fluctuate in concentration in relation to the flowering cycle that are not flowering regulators, but these compounds can be separated from the flowering regulators through the use of routine screening procedures. The advantage of our method is that this screening step, which has been protracted and unreliable in previous methods, is reduced to a simple, final screening step.

The plant extracts referred to above are preferably prepared by disintegrating the fresh plant tissue in methanol or acetone, evaporating the solvent until only a precipitate and an aqueous solution of plant material remains, and then resuspending the material in methylene chloride.

The flowering inhibiting regulator BEHD has active analogs. These analogs are diesters of dicarboxylic acids, which acids contain from 2 to 16 carbon atoms, the diesters of these acids having as one alcohol residue an alkyl radical containing from 3 to 16 carbon atoms and having as the other alcohol residue an alkyl radical containing from 3 to 16 carbon atoms. These compounds may also be used to promote vegetative growth in plants.

BRIEF DESCRIPTION OF THE DRAWINGS

Other objects, advantages and features of the invention will become more readily apparent upon consideration of the following detailed description of the invention in conjunction with the accompanying drawings, wherein:

FIG. 3 illustrates the identification of BEHD by mass spectroscopy (left) and high resolution gas chromatography (right). On the right, the relative retention time (RRT) of the unknown compound (upper trace) is compared to the RRT's of BEHD (arrow and left hand peak of the lower trace) and its isomers (lower trace): Bis-(4-ethyhexyl) hexane dioate (center peak) and bis(octyl) hexane dioate (right hand peak). On the left, the fragmentation pattern of the mass spectrum of the unknown compound (upper) is compared to that of authentic BEHD (lower). The structure of BEHD is given with the lower left-hand trace.

FIG. 4 is an illustration of a gas chromatogram similar to FIG. 2, with an arrow indicating a second compound present in uninduced plants only.

DETAILED DESCRIPTION OF THE INVENTION

Figure 1:
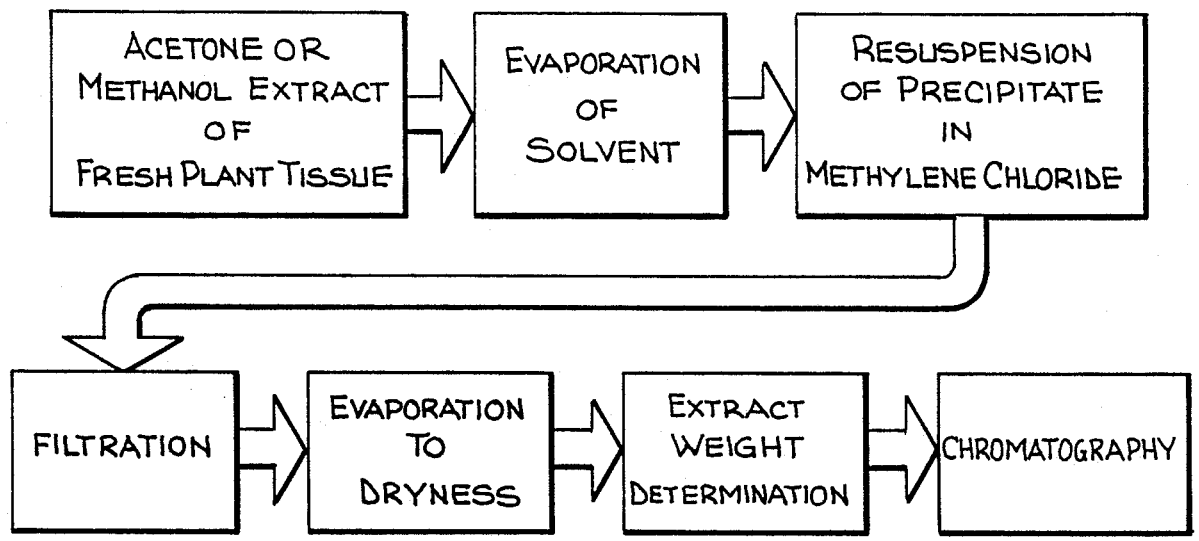
FIG. 1 is a schematic chart summarizing the procedure for preparing extracts of plant tissue used to identify flowering inhibiting regulators.

Our invention includes the following aspects: the discovery of a flowering inhibiting regulator (By "regulator," we mean a compound endogenous to or naturally occurring in plants which is a part of the mechanism controlling flowering in plants); the provision of a method of identifying flowering regulators; the development of a family of similar compounds which have flowering inhibiting activity; and the application of the flowering inhibiting regulator to delay flowering in plants. Each of these aspect will be explained in detail below.

We have discovered that bis (2-ethylhexyl) hexane dioate (BEHD) is a flowering inhibiting regulator. Plants control flowering, at least in part, by producing this regulator during those periods of the growth cycle of the plant when flowering does not occur. At that point in the growth cycle of the plant when the regulator is no longer produced by the plant, the flowering inhibiting effect of the regulator will decrease, and the plant will flower. The time at which the inhibitory regulator is no longer produced ("no longer produced" is herein intended to encompass a decrease in production to a point at which the regulator is no longer effective, or an increase in the rate at which the regulator is inactivated by or cleared from the plant) is the time of the year at which the plant is induced to flower or is otherwise capable of flowering.

Out method of identifying flowering regulators did not employ a test for flowering inhibiting activity on live plants (a "bioassay") until the regulator was (a) determined to be present in plants, (b) determined to fluctuate in concentration with the flowering cycle of the plants, and (c) the structure of the regulator identified. This is a reverse approach from all previously reported methods of which we are aware, in which protracted bioassays are used to screen crude plant extracts containing numerous compounds. In our procedure, a leaf tissue sample was collected from a group of plants which had been induced to flower, and a second tissue sample was collected from a groups of like plants of the same age which had not been induced to flower. Extracts were prepared from each of these tissued samples, and chromatograms obtained from each of these extracts with high resolution gas chromatography (HRGC). These two chromatograms were then compared to detect peaks which were present in one sample but not in the other. When such a peak was detected, the compound which caused that peak was identified through the use of combined gas chromatography-mass spectrophotometry (GC-MS). With this procedure, which will be set out in greater detail in the examples below, we identified BEHD as a flowering inhibiting regulator.

This same method can be used to identify other compounds which are flowering regulators. While it may be that some compounds identified by this method will not be active flowering regulators, the active compounds can easily be distinguished from the inactive compounds through the use of routine screening procedures, such as the screening procedure used by us and set forth herein.

The extracts of the plant tissue can be prepared by extracting the plant tissue in a solvent such as acetone or methanol, evaporating the solvent until only a precipitate and an aqueous solution remain, and resuspending the precipitated material in methylene chloride. This procedure provides an extract which is in a form suitable for HRGC analysis without requiring the use of numerous steps.

Chemicals which have structures similar to BEHD are also suitable for delaying flowering in plants. These compounds are diesters of dicarboxylic acids. The acid portion of these compounds should contain from 2 to 16 carbon atoms, or more preferably 2 to 8 carbons. Each of the alcohol residues should be a substituted or unsubstituted alkyl radical having from 3 to 16 carbon atoms, or more preferably 4 to 10 carbons. Each alkyl radical comprising one of the alcohol residues may be different from the other. These compounds are broadly useful in treating plants, and can be used to promote vegetative growth in plants and as an insecticide or insect repellent on plants. Specific examples of these compounds will be set forth in the examples below.

The compounds of the present invention can be applied to plants by any means so long as they are applied to the leaves of the plants. They may be applied alone, or in combination with inert solids such as a dust, or, preferably, suspended in a liquid solution such as water.

In place of water of in addition to, there can be employed organic solvents as carriers, e.g., hydrocarbons such as benzene, toluene, xylene, kerosene, diesel oil, fuel oil and petroleum naphtha, ketones such as acetone, methyl ethyl ketone and cyclohexanone, chlorinated hydrocarbons such as carbon tetrachloride, chloroform, trichloroethylene and perchloroethylene, esters such as ethyl acetate, amyl acetate and butyl acetate, ethers, e.g., ethylene glycol monomethyl ether and diethylene glycol monomethyl ether, alcohols, e.g., ethanol, methanol, isopropanol, amyl alcohol, ethylene glycol, propylene glycol, butyl carbitol acetate and glycerine. Mixtures of water and organic solvents, either as solutions or emulsions, can be employed.

The compounds can also be applied as aerosols, e.g., by dispersing them in air by means of a compressed gas such as dichlorodifluoromethane or trichlorofluoromethane and other Freons, for example.

The compounds of the present invention can also be applied with adjuvants or carriers such as talc, pyrophyllite, synthetic fine silica, attapulgus clay (attaclay), kieselguhr, chalk, diatomaceous earth, lime, calcium carbonate, bentonite, fuller's earth, cottonseed hulls, wheat flour, soybean flour pumice, cottonseed hulls, wheat flour, soybean flour pumice, tripoli, wood flour, walnut shell flour, redwood flour and lignin.

It is frequently desirable to incorporate a wetting agent in the compositions of the present invention. Such wetting agents are advantageously employed in both the solid and liquid compositions. The wetting agent can be anionic, cationic or nonionic in character.

Typical classes of wetting agents include alkyl sulfonate salts, alkylaryl sulfonate salts, alkyl sulfate salts, alkylamide sulfonate salts, alkylaryl polyether alcohols, fatty acid esters of polyhydric alcohols and the alkylene oxide addition products of such esters, and addition products of long chain mercaptans and alkylene oxides. Typical examples of such wetting agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid (di-2-ethylhexyl), ester of sodium sulfosuccinic acid, sodium lauryl sulfate, sodium salt of the sulfonated monoglyceride of cocoanut fatty acids, sorbitan, sesquioleate, lauryl trimethyl ammonium chloride, octadecyl trimethyl ammonium chloride, polyethylene glycol lauryl ether, polyethylene esters of fatty acids and rosin acids, e.g., Ethofat 7 and 13, sodium N-methyl-N-oleyltaurate, Turkey Red oil, sodium dibutylnaphthalene sulfonate, sodium lignin sulfonate (Marasperse N), polyethylene glycol stearate, sodium dodecylbenzene sulfonate, tertiary dodecyl polyethylene glycol thioether (Nonionic 218), long chain ethylene oxide-propylene oxide condensation products, e.g., Pluronic 61 (molecular weight 1,000), sorbitan sesquioleate, polyethylene glycol ester of tall oil acids, sodium octyl phenoxyethoxyethyl sulfate, polyoxyethylene (20) sorbitan monolaurate ("Tween 20"), tris (polyoxyethylene) sorbitan monostearate ("Tween 60"), and sodium dihexyl sulfosuccinate.

The solid and liquid formulations can be prepared by any of the conventional procedures. Thus, the active ingredient, in finely divided form if a solid, may be tumbled together with finely divided solid carrier. Alternatively, the active ingredient in liquid form, including solutions, dispersions, emulsions and suspensions thereof, may be admixed with the solid carrier in finely divided form.

The concept which is the present invention can be embodied in numerous different forms. The following examples are presented to illustrate some of these different embodiments.

EXAMPLE 1

This example illustrates the preparation of extracts from induced and uninduced plants, the detection of native plant compounds which fluctuate in concentration in relation to the flowering cycle of the plant, the identification of a flowering inhibiting regulator by gas chromatography, and the indentification of a flowering inhibiting regulator by combined gas chromatography-mass spectrophotometry (GC-MS).

a. Plant Materials and Growth Conditions

Seeds of Japanese Morning Glory (*Pharbitis nil* Choisy cv Violet) (Murasaki in Japanese) were obtained from Marutane Company Ltd. Shimogyoku, Kyoto, Japan.

Seventy seeds each were counted into a 50-ml beaker and combined with 40 ml of sulfuric acid for 30 minutes, and then rinsed under running tap water for 20 hours to soften the seeds coats. For most experiments, the seeds were planted, 15 per 15 centimeter pot containing a sterile potting medium such as "Premier Pro Mix" (Wyatt-Quarles, Raleigh, North Carolina). Seeds were arranged on the top of damp compressed potting medium and covered with 1-2 cm of fine vermiculate, also purchased from Wyatt-Quarles. Seed-containing pots were then placed in subirrigation trays filled with 1-2 cm of water and placed in the growth chamber.

The large growth chamber used was designed for precise control of temperature and relative humidity. For these experiments, the temperature was maintained at 24°±1.5° C. and the relative humidity at 65±5%. This chamber also contained 24 ceiling-mounted light fixtures, fitted with Sylvania "Gro-Lux" 40 watt plant lights. In addition, each shelf rack supported a 4-bulb fluorescent fixture also fitted with Sylvania "Gro-Lux" bulbs, suspended 18 inches above bench height. These lights provided a luminous flux density (illuminance) at plant height of approximately 17.09 W·m$^{-1}$ (400–850 nm) of the light period, and 0.52 W·m$^{-2}$ (400–800 nm) for a night break, as explained below.

All plants were grown in the large growth chamber under an 8-hour light/16-hour dark regime with a 2-hour low intensity night break starting at the seventh hour of the dark period. Some plants were exposed to the night break (short nights, SN). These constituted the noninduced plants and did not flower. Other plants received a long night; this was accomplished by placing them in a smaller light-tight growth cabinet in the large growth chamber at the end of the light period and thereby blocking them from receiving the night break. This treatment constituted long night conditions which are inductive for short day plants. Extra plants kept in both conditions were included to verify the flowering response.

The seedlings emerged on the third day after planting. Usually about half had trouble shedding their seed coat. This was corrected by misting the seedlings with temperature equilibrated tap water, which softened the seed coat and allowed its easy removal by hand. In the following 2 days, the seed leaves, or "cotyledons," opened, expanded, and achieved normal green color.

b. Extraction Procedure

This procedure can be best understood by referring to FIG. 1 in conjunction with the following text. The purpose of this procedure was to remove the water from the sample so that the sample could be injected into the chromatograph. Plants were harvested early in the mornning of the sixth day, just after the start of the light period. Intact cotyledons were removed from the plants and transferred to a clean, solvent rinsed 500-ml beaker. 50 ml of acetone (in other experiments, we found methanol to work also) were added for each gram of cotyledon tissue for a total of 200–500 mls of solvent, and the cotyledons were extracted therein until they disintegrated (1 hour). This disintegration process could optionally be facilitated by other conventional means, such as homogenization. All glassware was double washed and rinsed with the extracting solvent prior to use. The highest quality distilled-in-glass solvents were used.

Following the 1-hour extraction period, the acetone was evaporated under a vacuum until only a small amount of water and precipitated sample material remained. The water alone was then pipeted into a test tube, to which double the volume of methylene chloride was then added, forming 2 layers. The contents of the tube were then mixed thoroughly and allowed to separate. The top (pink-colored) water layer was then transferred to a clean dry preweighed test tube. The precipitated sample material was resuspended in methylene chloride and combined with the methylene chloride fraction remaining from the water partition. This sample was then evaporated to dryness for weight determination.

The dried sample was then resuspended in methylene chloride and the volume of the solvent adjusted so that a final sample concentration of 10 milligrams of sample per milliliter of solvent was obtained.

c. Chromatographic Procedures

The chromotographic system used was a Hewlett-Packard 5880-A level 4, dual capillary F.I.D. gas chromatograph. We used a 25-meter bonded methylphenyl-silicone (95% methyl, 5% phenyl) column with a 0.1 micron film thickness obtained from J & W Scientific Company (Rancho Cordova, California) under the designation "DB-5." The injection volume was 1.0 microliters. Ultra pure helium was used as the carrier gas at a flow rate of 4 milliliters per minute.

We used an injection technique referred to as the "splitless injection" method. It is called a splitless injection method because the injector split does not divide the vaporized sample as in standard capillary inlet system. In this technique, the carrier gas flow through the injector port is not divided but exits only into the column carrying with it the vaporized sample. This situation exists only during the injection and a short time (so seconds) after. Then the gas flow system is switched over to the split mode and the injector port is vented to purge excess solvent and eliminate an extended solvent tail. Splitless injections through hot injector ports into cool columns have the advantage of being able to focus the sample components due to the solvent effect proposed by Grob and Grob *J. Chrom. Sci.* 7, 587 (1969) as well as by sample cold trapping as explained by Freeman. *High Resolution Gas Chromatography,* 2d Ed. (R. R. Freeman, Ed. (1981). To augment this sample introduction technique a multilevel oven temperature program was used. An initial temperature of 40° C. was held for injection. The first oven temperature program rate of 10° C. per minute was used until 120° C. was reached, after which a program rate of 4° C. per minute was used until the final temperature of 280° C. was attained. Our protocol was such that the samples were chromatographed on the same day as collected. Same-day chromatography is an important advantage of our method, as it serves to avoid potential volatility of compounds and other storage artifacts.

Cotyledons form both induced and uninduced plants were raised, extracted, and chromatographed according to the foregoing procedure. The chromatogram for the uninduced tissue is displayed in the lower trace of FIG. 2, and the chromatogram for induced tissue is displayed in the upper trace of FIG. 2. The arrow identifies a peak at about the 30.4 minute relative retention time (RRT) position (the time required for that particular compound to pass through the chromatography column) corresponding to a compound which is present in the uninduced tissue but not present in the induced tissue (see also Table 1). This method enabled us to discover, for the first time, the presence of a compound believed to be an endogenous flowering inhibiting regulator involved in the control mechanism of flowering, as flowering occurs immediately after the compound disappears from the plant.

d. Gas Chromatography-Mass Spectrophotometry

GC-MS was carried out on a system composed of a Hewlett-Packard 5890 gas chromatograph connected to a Varian MAT 112 mass spectrometer. The same column and conditions as above were used for the separation. The mass spectrometer was operated at a source temperature of 240° C. and an electron energy of 70 eV.

Figure 2:
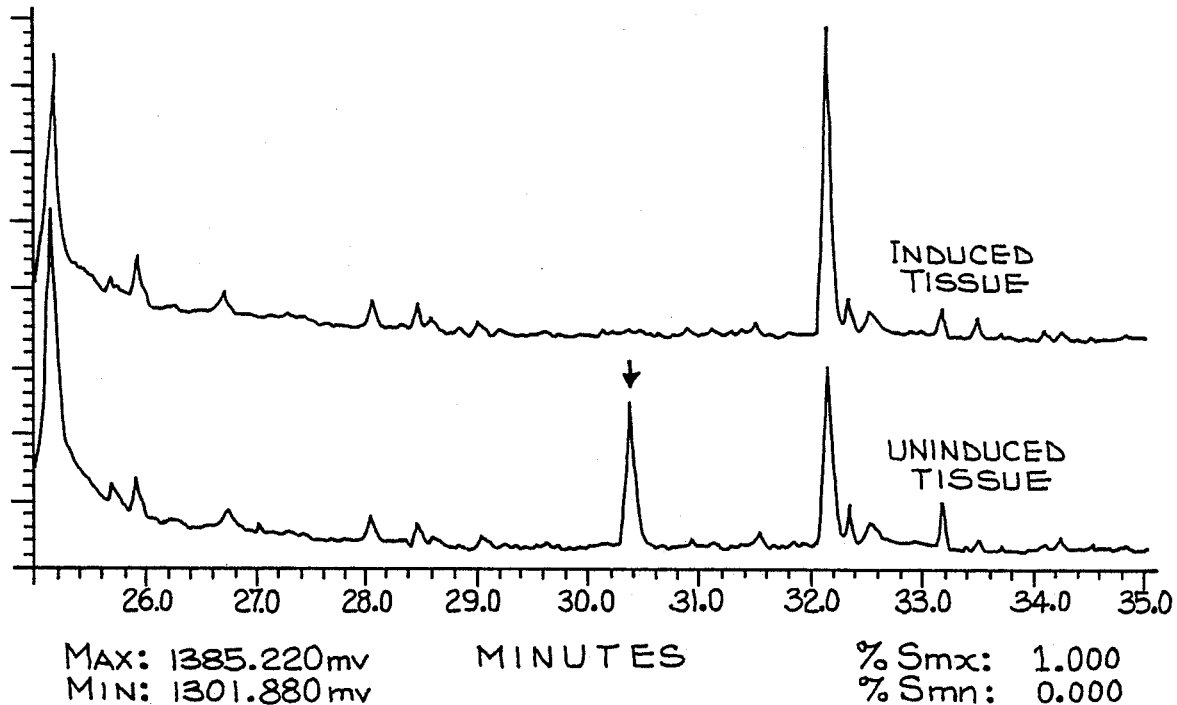
FIG. 2 is an illustration of a gas chromatogram of extracts from plants which have been induced to flower (top trace) and not induced to flower (bottom trace). The arrow indicates the peak caused by a flowering inhibiting regulator present only in uninduced plants.

Chromatographic analysis of an uninduced cotyledon tissue sample prepared according to the same method as was used to prepare the sample which produced the bottom trace of FIG. 2 provided a preliminary identification of the 30.4 minute peak as a hexanoic acid diooctyl ester (M.W. 370). Chromatography of bis (2-ethylhexyl) hexane dioate (BEHD), bis (4-ethylhexyl) hexane dioate, and bis (octyl) hexane dioate, as well as GC-MS, confirmed that the flowering inhibiting regulator was BEHD by demonstrating the similarity in retention time between BEHD and the flowering inhibiting regulator. The left side of FIG. 3 shows the mass spectrograph for the flowering inhibiting regulator obtained by GC-MS in the upper trace, and the mass spectrograph for BEHD in the lower trace. The degree of correlation between the two spectrographs is very high. The insert shows the structure of BEHD.

TABLE 1

| Peak Identification | Number of Long Night Inductions | Average Peak Area of 10 mg/ml Sample |
|---|---|---|
| (1) Pharbitis (Underivatized) | 0 | 68.64 |
| | 1 | 16.27 |
| | 2 | * |
| (2) Pharbitis (TMS Derivatized) | 0 | 10.78 |
| | 1 | * |
| | 2 | * |
| (3) Goosefoot (Underivatized) | 0 | 11.13 |
| | 3 | 88.91 |
| | 5 | 125.8 |

*Indicates below detectable limits

EXAMPLE 2

This example is similar to example 1, and illustrates the detection of a second compound which is present in uninduced Morning Glory and is absent from induced Morning Glory. The procedure is similar to the procedure used in example 1, except that a derivatization step was added to increase the volatility of the sample.

The dried samples described in subsection "b" of example 1 were suspended in derivatizing reagent instead of methylene chloride. The derivatizing reagent was made up by mixing 90 ml pyridine, 10 ml bis (trimethysilyl)-trifluoro acetamide (BSTFA) and 1 ml of trimethylchlorosilane (TMCS), all obtained form Regis Chemical of Morton Grove, Illinois. Derivatization of this type produced trimethylsilyl derivatives of all available hydroxyl groups and greatly increased the volatility of the compounds being chromatographed. Samples to be derivatized were heated in a dry block bath to 75° C. for 30 minutes, after which the internal standard (n-nonadecane in hexane) was added just prior to chromatography.

The analysis procedure for derivatized samples used a temperature programmed run from 140°–280° C. at 4° C. per minute. Split type injection was standard (Freeman, supra, 1981). The injector temperature was 270° C. and the detector temperature was 290° C.

Analysis of this extract revealed a peak with a RRT of about 21.1 minutes which can be found only in uninduced cotyledon tissue (see FIG. 3 and Table 1).

When crude cotyledon extracts containing this compound were partitioned between methanol and hexane, the compound was found to be soluble in the methanol fraction. The compound identified in example 1, however, was found to be soluble in the hexane fraction. This example therefore demonstrates that this procedure can be used to extract and identify a variety of different compounds which fluctuate in concentration in relation to the flowering cycle.

EXAMPLE 3

This example is similar to examples 1 and 2, except it was carried out with Goosefoot (*Chenopodium rubrum*).

Seeds of Chenopodium rubrum strain 374, a qualitative short day plant, were obtained from J. Krekule, Czechoslovak Acad. Sciences, Prague. Uniform germination was promoted by soaking the seeds in cool water (10°–12° C.) for 12 hours, then soaking the seeds in warm water (30° C.) for 12 hours, and then again soaking the seeds in cool water for 12 hours.

Selected plantlets were cultivated in vermiculite at 25° C. under continuous light. After 21 days the plants were subjected to inductive photoperiods (10 hours light/14 hours dark) for 1–5 days. Noninduced plants were kept under continuous light.

A peak that exhibits a great increase in response to inductive conditions comes from *Chenopodium rubrum*. It was found in underivatized acetone extracts and visualized when chromatographed using splitless injection and multilevel temperature programming as described in example 1. In contrast to the other two peaks, this peak (RRT 52.5 minutes) increases dramatically upon induction, the amount of increase being proportional to the number of inductive cycles (see FIG. 4 and Table 1). This compound may therefore be a flowering promoting regulator.

This example demonstrates that the procedures described in examples 1 and 2 can be carried out with different species of plants, and can be used to detect native plant compounds which increase in concentration in response to the induction of flowering.

EXAMPLES 4–10

These seven examples demonstrate the great variety of plants for which BEHD can be used as a flowering inhibiting regulator.

Example 4 was carried out with Morning Glory. The plants were raised until they were 6 days old, and then given up to 2 inductive long nights. The short night regime was an 8-hour photoperiod followed by a 16-hour scotoperiod; the scotoperiod was interrupted by a 1-hour light break immediately after the seventh hour.

Example 5 was carried out with Cockleburr (*Xanthium strumarium*). The plants were given up to 2 inductive longer nights when they were 35 days old. The plants were given short night cycles of 20 hours light and 4 hours darkness; the inductive long night cycles were 8 hours light and 16 hours darkness.

Example 6 was carried out with Goosefoot (*Chenopodium rubrum*). The plants were given up to 5 inductive long nights when they were 21 days old. They were given continuous light for their short night cycles; the inductive long night cycles were 16 hours of light followed by 8 hours of darkness.

Examples 7–10 were carried out with Impatiens (*Impatiens balsamina*), Cucumber (*Cucumis sativus*), Pea (*Pisum sativum*) of both Alaska and Progress No 9 strains, and Bean (*Phaseolus vugaris*) which were grown at intervals in a greenhouse from early spring through late summer. In each example, a dilute aqueous solution of 0.1 millimolar BEHD was prepared in 30% acetone, with 0.01% "Tween-20" as a wetting agent. This solution was applied by spraying it onto whole plants until runoff; control plants were sprayed with the same solution lacking BEHD. Spraying of the Morning Glory, Cockleburr, and Goosefoot began 1 day before the first inductive short day period, continued through 2 days of inductive short days, and continued daily or on alternate days for an additional week of long days. All of the other species were sprayed daily from 2 weeks after planting until the time of harvest. The total time, from planting to harvest, ranged from 37 days for Morning Glory to 76 days for Impatiens. The results of these treatments are set forth in Table 2.

These examples show that BEHD has a pronounced inhibitory effect on flowering in a diverse variety of plants at even a very dilute concentration. Not only are these plants of varied species, but four of them (cucumber, pea, bean, and tobacco) were day neutral plants (DNP).

EXAMPLE 11

This example provides a further demonstration of the power of the flowering inhibiting effect of BEHD. The procedure followed was a similar to the procedures used in examples 2–8, except that BEHD was applied to a day neutral variety of tobacco (*Nicotani tobaccum* cv. xanthi), and the concentration of the BEHD was one-tenth of that used in previous experiments. The BEHD was applied daily for 6 consecutive days after the plants were 2.5 months old. As a result of these applications, the flowering of the tobacco plants was almost completely inhibited (See Table 2).

TABLE 2

| PLANT TYPE | PLANT | AMOUNT OF FLOWERING | | INHIBITION (%) |
|---|---|---|---|---|
| | | CONTROL | BEHD | |
| SDP | (4) MORNING GLORY (P) | 8.5 ± 1.2 | 5.2 ± 1.2 | 39% |
| | (5) COCKLEBURR (S) | 5.3 ± 0.2 | 1.5 ± 0.4 | 72% |
| | (6) GOOSEFOOT | 6.8 ± 0.2 | 4.5 ± 0.2 | 34% |
| | (7) IMPATIENS (P) | 17.3 ± 1.7 | 10.4 ± 0.5 | 40% |
| DNP | (8) CUCUMBER (P) | 26.1 ± 0.4 | 17.4 ± 0.2 | 33% |
| | (9) PEA (N) | | | |
| | cv. Alaska | 1.0 ± 0.3 | 0.6 ± 0.2 | 35% |
| | cv. Progress #9 | 1.0 ± 0.6 | 0.6 ± 0.3 | 45% |
| | (10) BEAN (P) | 18.2 ± 1.7 | 8.0 ± 3.4 | 56% |
| | (11) TOBACCO (P) | 1.0 ± 0.0 | 0.0 ± 0.0 | 90% |
| LDP | (12) MUSTARD | 1.0 ± 0.6 | 0.0 ± 0.0 | 100% |

EXAMPLE 12

This example demonstrates that BEHD can inhibit flowering in long day plants, as well as in short day and day neutral plants. The procedure was similar to the procedures set forth in examples 4–11, except that the BEHD was applied to the long day plant (LPD) mustard (*Sinapsis alba*). As a result, the flowering of the mustard was completely inhibited (See Table 2). We have also found BEHD to have a flowering inhibiting effect in preliminary experiments on Cauliflower (*Brasica oleracea* L., cv. botrytis) and Broccoli (*Brasica oleracea* L., cv. botrytis), which are also long day plants. This example illustrates the power of the inhibitory effect of BEHD, as well as the diversity of plants on which BEHD has a flowering inhibiting action.

EXAMPLE 13

We have conducted a dose-response study with BEHD on Morning Glory according to the foregoing procedures. The results of this study indicate that the preferred concentration of BEHD for achieving an inhibitory effect on flowering is from 0.01 to 1.0 millimolar, with a concentration of from 0.1 to 0.5 millimolar being most preferred.

EXAMPLE 14

Figures 5, 6:
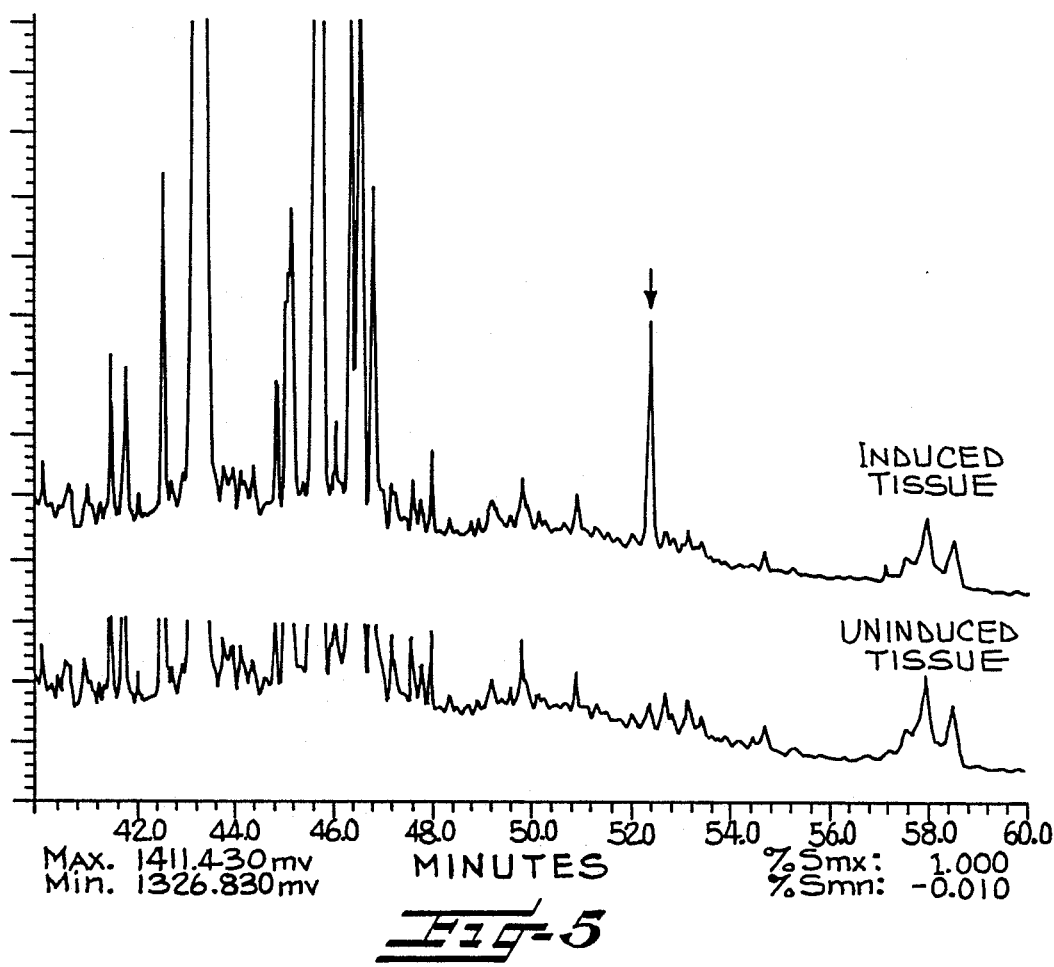
FIG. 5 is an illustration of a gas chromatogram like FIGS. 1 and 2, with the arrow indicating a compound which greatly increases in concentration upon the induction of flowering.
FIG. 6 illustrates the effects of inductive long nights on the BEHD content of morning glory cotyledons (A), cockleburr leaves (B) or goosefoot leaves (C). The figures on the left show representative chromatograms derived from short night controls (upper traces) and from long night induced material (lower traces). In the first tabular column are given either the number of long nights (1, 2 or 5) or their temporally matched short night controls (0). The second tabular column shows the computed BEHD concentrations of cotyledons or leaves (average of 4–5 experiments). The last tabular column shows the amount of flowering induced by the long nights in companion plants to those shown in the previous column. The measures of flowering were computed as the number of flowers per plant (P) or the flowering stage (S).

This example illustrates how the concentration of BEHD in Morning Glory decreases over time in response to long night induction of flowering, and demonstrates that the time at about which BEHD should be applied to the plant in order to prolong the duration of the inhibitory effect of the regulator on the plant is the time when the plant is induced to flower. The procedure employed was the same as the procedure set forth in example 1, except the plants were raised according to the procedure used in example 4, and were thus not given a long night until they were old enough to be induced. Referring to FIG. 6, row A, in the left column is shown the HRGC trace for uninduced (top) and 2-day induced (bottom) cotyledon tissue. The traces again show the disappearance of the BEHD trace after induction. The shift in relative retention time for the BEHD as compared to example 1 results from the use of different HRGC equipment. The right column of FIG. 6, row A, provides a table comparing the number of long night induction days received by the plants being analyzed, the concentration of BEHD per gram of fresh tissue in those plants, and the percentage of flowering expressed by those plants. This table shows that the degree of flowering is inversely related to the concentration of BEHD present in the plant.

This example shows that flowering in Pharbitis could be inhibited by supplying the plant with additional BEHD at about the time when BEHD is no longer being produced. Because the plant is still in a vegetative state at this time (before the conversion of vegetative, leaf-producing buds to floral buds), this method can therefore be used to inhibit flowering by applying BEHD to the plants while the plants are still in a vegetative state and thereby serves to maintain the plants in a vegetative state. The precise time when the BEHD should be supplied is dependent upon the degree of inhibition which is desire; if maximum inhibition is desired, the BEHD should be supplied before the concentration of BEHD in the plant has dropped significantly. If lesser amounts of inhibition can be tolerated, the BEHD could be applied later, even after the BEHD concentration in the plant has decreased significantly. Similarly, the amount of BEHD which should be supplied to the plant will depend on the degree of inhibition desired.

EXAMPLE 15

This example further demonstrates our discovery that the time at about which BEHD is no longer produced by a plant is the time when the plant is induced to flower. The procedure was similar to example 14, except that is was carried out with Cockleburr. Plants were raised according to the procedure used for example 5. The left column of FIG. 6, row B, again demonstrates the presence of BEHD in uninduced and its absence in induced plants. The accompanying table again demonstrates the inverse relation between BEHD concentration and degree of flowering. Similar to example 4, this example shows how flowering in Cockleburr could be inhibited by supplying the plant with additional BEHD at about the time when BEHD is no longer being produced by the plant.

EXAMPLE 16

This example provides a still further demonstration of the time about which BEHD is no longer produced. The procedure was similar to that used in example 14, except it was carried out with Goosefoot. Plants were raised according to the procedure used for example 6. The left column of FIG. 6, row C, again demonstrates the presence of BEHD in uninduced plants and its reduction in induced plants. The accompanying table again demonstrates the inverse relation between BEHD concentration and degree of flowering. Similar to examples 4 and 5, this example shows how flowering in Goosefoot could be inhibited by supplying the plant with additional BEHD at about the time when BEHD is no longer being produced by the plant. For the purposes of this invention, the phrase "no longer being produced" is intended to encompass those situations where BEHD is only being produced in a reduced amount, the reduction being such that the percentage of flowering is caused to increase, or those situations in which BEHD is more rapidly inactivated by or cleared from the plant.

The teachings provided by these specific examples will enable those skilled in the art to practice our invention on other species of plants not specifically set forth herein through the application of knowledge common in the field. More specifically, those skilled in the art know the time or year at which, or photoperiods under which, different species of plants are induced to flower at various temperatures and latitudes, or the conditions under which day neutral plants are otherwise capable of flowering, and can combine this information with the teachings contained herein to practice the invention. Much of this information has, for example, been gathered in the *CRC Handbook of Flowering*, A. H. Halevy, Ed., CRC Press, Inc., Boca Raton, Florida, ISBN-0-8493-3911-1 (1985).

Taken together, examples 14, 15 and 16 also demonstrate that BEHD is not a regulator which is present only in a single species of plant; rather, it is present and functioning in broadly divergent plant species. This confirms the demonstration that BEHD is a flowering inhibiting regulator provided in examples 4–12 above.

EXAMPLES 17 and 18

These examples further clarify that it is the time at about which the flowering inhibiting regulator is no longer being produced by a plant when BEHD should be applied to the plant to inhibit flowering. The procedure used in these examples was the same as the procedure used in examples 4 through 10, except only Morning Glory and Impatiens were used, and, unlike the procedure in the earlier examples, the aqueous solution of BEHD was applied only on those days when the plants were receiving inductive long nights. This treatment resulted in the inhibition of flowering to almost the same extent as continual spraying for 1 to 2 weeks (See Table 3).

TABLE 3

| | Percent Inhibition of Flowering | | |
|---|---|---|---|
| | Plant | 1 day | 8 days |
| (17) | Impatiens | 26% | 55% |
| (18) | Morning Glory | 28% | 35% |

While application of BEHD can begin before the time at about when it is no longer being produced by the plant, and such a treatment is encompassed by the present invention, such early initiation of treatment would be of little benefit as the early applications would have a lesser effect on the plants being treated.

EXAMPLES 19–24

These examples demonstrate that the compounds having structures similar to BEHD also have flowering inhibiting activity.

The procedure was carried out on Morning Glories and was the same as the procedure of example 4, except that in examples 20 through 24, different compounds were substituted for BEHD in the spray solution. A test of BEHD was repeated in example 16 to facilitate the comparison of the activity of BEHD with the activity of these other compounds. The results of these treatments are set forth in Table 4.

TABLE 4

| COMPOUND | FLOWERING OF MORNING GLORY (% INHIBITION) |
|---|---|
| (19) bis(2-ethylhexyl) hexane dioate (BEHD) | 45 |
| (20) bis(2-ethylbutyl) hexane dioate | 6 |
| (21) is(2-ethylhexyl) phthalate | 26 |
| (22) bis(4-ethylhexyl) hexane dioate | 30 |
| (23) bis octylhexane dioate, or dioctylhexane dioate | 24 |
| (24) dihexyl hexane dioate | −4 |

The compounds screened for activity above all had flowering inhibiting activity, with the apparent exception of dihexyl hexane dioate. Examination of the activities of these exemplary compounds will enable those skilled in the art to identify those compounds within the scope of the present invention having the greatest activity.

These compounds may be prepared by any of a number of procedures well known to those skilled in the art, such as by the procedures disclosed in U.S. Pat. No. 2,508,911, the contents of which is incorporated herein by reference.

EXAMPLES 25–26

These examples demonstrate that BEHD can be used to promote vegetative growth in plants.

During the treatments described in examples 5–8, it was observed that the bean and impatiens plants grew more and produced larger, darker green leaves than those plants which were sprayed with the control solution. BEHD can thus be used as a plant growth regulator which promotes vegetative growth, in addition to its use as a flowering inhibiting regulator.

EXAMPLES 27-30

It has been suggested that some compounds which are naturally occurring in plants serve as insecticides ("insecticide" as used herein is intended to encompass both compounds which repel insets and compounds which kill insects). For example, it has been suggested that methylxanthines such as caffeine are naturally occurring insecticides. Nathanson, Science, 226, 184 (Oct. 12, 1984). We have discovered that BEHD is such a naturally occurring insecticide.

Whiteflies are a terrible problem for many greenhouse and field crops. They are very hard to get rid of, usually requiring very toxic insecticides. We completed experiments on 4 species of plants which were either sprayed with $10^{-4}$M. BEHD or with control solutions. Table 5 shows that in all 4 cases, there were many less whiteflies infesting the BEHD-treated plants than the controls.

TABLE 5

| PLANT | WHITEFLIES PER LEAF | | % INHIBITION |
| --- | --- | --- | --- |
|  | CONTROL | BEHD |  |
| (27) Bean | 28 ± 3 | 4 ± 1 | 86 |
| (28) Cauliflower | 20 ± 2 | 10 ± 1 | 50 |
| (29) Mustard | 42 ± 5 | 10 ± 2 | 77 |
| (30) Broccoli | 15 ± 1 | 8 ± 1 | 48 |

Thus BEHD can also be used to control insect damage to plants.

The foregoing embodiments are considered to be illustrative rather than restrictive of the invention, and those modifications which come within the meaning and range of equivalents of the claims are to be included therein.

That which is claimed is:

1. A method of treating plants in a non-toxic manner to control flowering without killing or damaging the plant, which method comprises applying to the plants a solution of a diester of a dicarboxylic acid, which acid contains from 2 to 16 carbon atoms, said diester having as one alcohol residue an alkyl radical containing from 3 to 16 carbon atoms, and having as the other alcohol residue an alkyl radical containing from 3 to 16 carbon atoms, in an amount insufficient to kill but effective to delay the flowering of said plants.

2. A method of delaying the conversion of vegetative buds to floral buds in plants which comprises applying to a plant an amount insufficient to kill but effective to delay the conversion of vegetative buds to floral buds of a diester of a dicarboxylic acid, which acid contains from 2 to 16 carbon atoms, said diester having as one alcohol residue an alkyl radical containing from 3 to 16 carbon atoms, and having as the other alcohol residue an alkyl radical containing from 3 to 16 carbon atoms.

3. A method of delaying the conversion of vegetative buds to floral buds in a plant which controls its flowering by producing a flowering inhibiting regulator, comprising applying a non-toxic amount insufficient to kill but effective to delay the conversion of vegetative buds to floral buds of a diester of a dicarboxylic acid to said plant about the time in the growth cycle of said plant when said regulator is no longer produced by the plant, wherein said acid contains from 2 to 16 carbon atoms, and wherein said diester has as one alcohol residue an alkyl radical containing from 3 to 16 carbon atoms and has as the other alcohol residue an alkyl radical containing from 3 to 16 carbon atoms.

4. A method of delaying the conversion of vegetative buds to floral buds in plants comprising applying to said plants while said plants are still in a vegetative state an amount insufficient to kill but effective to delay the conversion of vegetative buds to floral buds of a diester of a dicarboxylic acid, which acid contains from 2 to 16 carbon atoms, said diester having as one alcohol residue an alkyl radical containing from 3 to 16 carbon atoms, and having as the other alcohol residue an alkyl radical containing from 3 to 16 carbon atoms.

5. A method according to claim 1, 2 or 3, wherein said diester of a dicarboxylic acid is applied to said plant in an amount effective to delay the conversion of vegetative buds to floral buds and to promote vegetative growth.

6. A method according to claims 1, 2 or 3, wherein said diester of a dicarboxylic acid is bis (2-ethyhexyl) hexane dioate.

7. A method according to claims 1, 2, or 3, wherein said diester of a dicarboxylic acid is applied to said plant in a concentration of from 0.01 to 1.0 millimolar.

* * * * *

UNITED STATES PATENT AND TRADEMARK OFFICE
CERTIFICATE OF CORRECTION

PATENT NO. : 4,818,274

DATED : 4 April 1989

INVENTOR(S) : Kenneth A. Bridle and Mordecai J. Jaffe

It is certified that error appears in the above-identified patent and that said Letters Patent is hereby corrected as shown below:

Column 2, line 68, "naphthaleneaceticacid" should read --naphthaleneacetic acid--.

Column 6, line 37, "Out" should read --Our--.

Column 9, line 5, "$W \cdot m^{-1}$" should read --$W \cdot m^{-2}$--.

Column 9, line 6, "of the" should read --for the--.

Column 10, lines 19-20, "(so seconds)" should read --(30 seconds)--.

Column 11, lines 2-3, "diooctyl" should read --dioctyl--.

Column 11, lines 41-42, "trimethysilyl" should read --trimethylsilyl--.

Column 12, line 63, there should be a space between "Tween-20" and "as."

Column 13, line 50, "(LPD)" should read --(LDP)--.

Column 15, line 41, "or year" should read --of year--.

UNITED STATES PATENT AND TRADEMARK OFFICE
CERTIFICATE OF CORRECTION

PATENT NO. : 4,818,274

DATED : April 4, 1989

INVENTOR(S) : Kenneth A. Bridle and Mordecai J. Jaffe

It is certified that error appears in the above-identified patent and that said Letters Patent is hereby corrected as shown below:

Column 16, Table 4, line 39, "is" should read -- bis --.

Signed and Sealed this

Second Day of January, 1990

*Attest:*

JEFFREY M. SAMUELS

*Attesting Officer*     *Acting Commissioner of Patents and Trademarks*